United States Patent
Plüss-Wenzinger et al.

(10) Patent No.: US 6,312,942 B1
(45) Date of Patent: Nov. 6, 2001

(54) APPARATUS FOR ENCAPSULATING SUBSTANCES IN SMALL SPHERICAL PARTICLES FORMED FROM AN ENCAPSULATING FLUID

(75) Inventors: Raphael Plüss-Wenzinger, Schiers GR; Fritz Widmer, Zürich; Christoph Heinzen, Zollikon; Harry Brandenberger, Zürich, all of (CH)

(73) Assignee: Inotech AG, Dottikon (CH)

( * ) Notice: Subject to any disclaimer, the term of this patent is extended or adjusted under 35 U.S.C. 154(b) by 0 days.

(21) Appl. No.: 09/197,826

(22) Filed: Nov. 23, 1998

(30) Foreign Application Priority Data

Nov. 27, 1997 (DE) ............................................. 197 52 585

(51) Int. Cl.⁷ ............................. C12M 1/00; C12N 11/10; C12N 5/00; G01N 33/548; C07K 17/10
(52) U.S. Cl. ........................ 435/283.1; 435/178; 435/182; 435/382; 436/529; 436/535; 530/813; 530/817
(58) Field of Search ..................................... 435/177, 178, 435/182, 283.1, 289.1, 382; 436/529, 535; 530/813, 817

(56) References Cited

U.S. PATENT DOCUMENTS 5,460,943 * 10/1995 Hayashi et al. ........................ 435/7.4

FOREIGN PATENT DOCUMENTS

9628247 * 9/1996 (WO).

* cited by examiner

*Primary Examiner*—David M. Naff
(74) *Attorney, Agent, or Firm*—Bachman & LaPointe, P.C.

(57) ABSTRACT

Substances such as chemical substances and biological substances including animal, vegetable and microbial cells are encapsulated using a process and an apparatus wherein a coil through which alternating current flows causes a magnet to vibrate creating vibrations such as in the range of between 300 to 4000 Hz that are transmitted to an encapsulating fluid containing the substance to form small substantially spherical particles containing the substance. The apparatus includes a pulsation chamber containing a movable wall for receiving the encapsulating fluid containing the substance to be encapsulated. A nozzle is spaced downstream from the pulsation chamber for receiving the encapsulating fluid from the pulsation chamber. A permanent magnet is mounted on the movable wall, and a coil is spaced from the permanent magnet by an air gap and is located proximate to the permanent magnet. An alternating current source is connected to the coil for creating an alternating magnetic wave that causes vibration of the permanent magnet and wall attached thereto resulting in pulsing of the encapsulating fluid from the pulsation chamber through the nozzle to form the particles in which the substance is encapsulated.

3 Claims, 2 Drawing Sheets

APPARATUS FOR ENCAPSULATING SUBSTANCES IN SMALL SPHERICAL PARTICLES FORMED FROM AN ENCAPSULATING FLUID

BACKGROUND OF THE INVENTION

The present invention concerns a process and an apparatus for encapsulating microbial, vegetable and animal cells or biological and chemical substances through a nozzle into small, substantially spherical particles.

The encapsulation of microbial, vegetable and animal cells and biological and chemical substances such as catalysts is a matter of great significance in particular in biotechnology and medicine for immobilization purposes. In medicine encapsulation additionally serves to provide shielding from the immune system. By virtue of the immobilization effect, it is possible to retain the cells or the catalyst in the process and at the same time harvest the product. That makes it possible to achieve prolonged utility and an enhanced level of space-time yield. By virtue of the shielding effect for the cells from the immune system, it is possible to implant in a patient cells that are foreign to the patient's body and which over a prolonged period of time discharge a desired substance into the body of the patient without their being attacked and destroyed by the immune system of the patient.

The encapsulation of cells and catalysts in biopolymers such as carrageenan or alginate and synthetic polymers such as polyacrylamide is a method which has been used for some years in research laboratories. Many different apparatuses are described for that purpose in the literature. One of the most efficient methods involves dividing up a jet by the superimposition of an external oscillation or vibration on the immobilization fluid. That procedure provides that, as it is discharged from a nozzle in a laminar flow, the fluid is divided up into equal-sized fractions. A number of methods for vibration transmission are used or described, for example coupling to a vibrator, piezoelectric crystal, sound waves.

The applicants' WO 96/28247 shows a commercial encapsulation apparatus in which the vibration is transmitted by a rigid connection to a vibrator. That method suffers from the difficulty that the axis of the vibrator and the axis of the nozzle must be precisely aligned as otherwise disturbance phenomena occur, which have a massively adverse effect on the homogeneity of the sphere size. In addition the vibrator is expensive.

In consideration of that state of the art, the inventor set himself the aim of optimising an apparatus and a process of the kind set forth above.

SUMMARY OF THE INVENTION

In accordance with the process of the invention the immobilization mixture is divided into equal-sized fractions by the superimposition of an external vibration, wherein said vibrations are transmitted to the immobilization mixture either within a pulsation space or by way of the nozzle which is caused to pulsate.

The invention includes an apparatus in which a pulsation chamber which is arranged upstream of the nozzle and which accommodates the immobilization mixture is overlaid by a permanent magnet and the latter is arranged opposite an electric coil: one of the two units is provided in accordance with the invention within the pulsation chamber or on a diaphragm which spans over the pulsation chamber, while the other unit is separated from that associated with the pulsation chamber by an air gap.

In another embodiment of the apparatus, the permanent magnet and the electric coil are associated with the nozzle or the suspension means thereof so that it can introduce the pulsation effect.

In accordance with a further feature of the invention the permanent magnet and the coil through which alternating current flows generate vibrations in a preferred range of between 300 and 4000 Hz.

By virtue of the invention, using simple means, it is possible to miniaturize the vibration transmission means, with a very low level of expenditure in terms of material and energy. In that way the costs of the process and the apparatus can be reduced by a multiple in comparison with the previously known vibration processes.

The invention is essentially based on the fact that the principle of a vibrator comprising a magnet and a coil through which alternating current flows is taken out of the vibrator and a part thereof is associated directly with the pulsation chamber. If alternating current is passed through the coil, it is alternately positively and negatively magnetized. The magnetic waves interact with the magnet disposed therebeneath and cause it to vibrate. The vibrations are transmitted almost without resistance to the immobilization fluid.

A point which is to be deemed a further advantage is that alignment of the magnet and the coil does not have to be centered accurately to 0.1 mm. Also there are no axes which have to be exactly aligned.

BRIEF DESCRIPTION OF THE DRAWINGS

Further advantages, features and details of the invention will be apparent from the following description of a preferred embodiment and with reference to the drawing in which.

DETAILED DESCRIPTION

Figure 1:
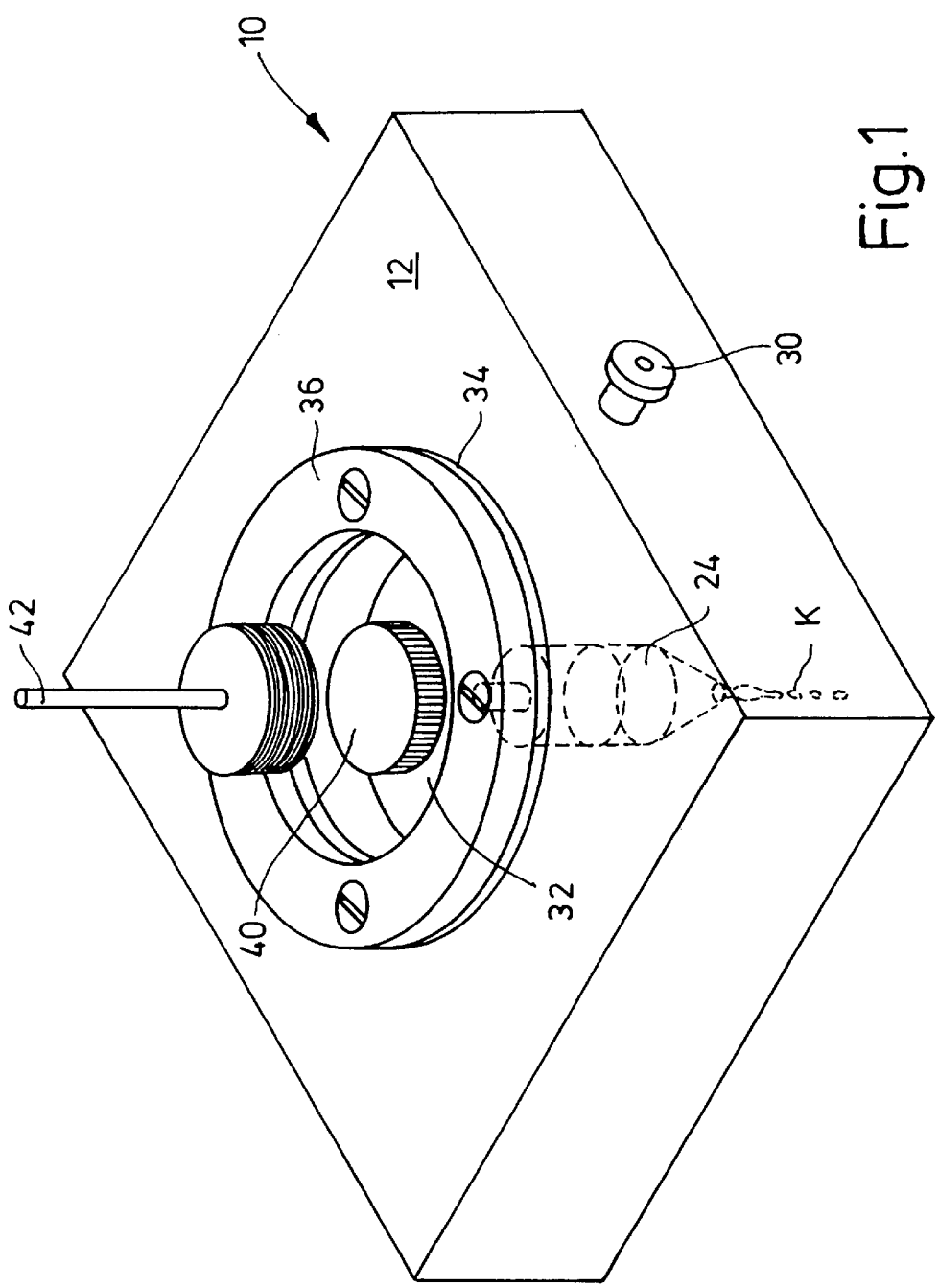
FIG. 1 is a perspective view of an apparatus according to the invention.
Figure 2:
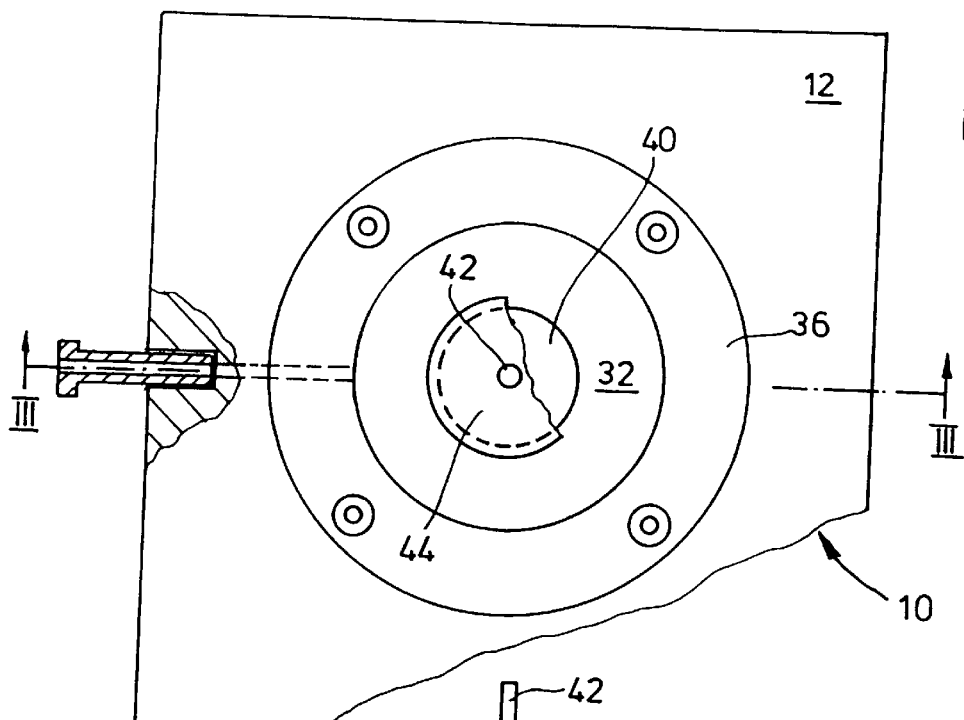
FIG. 2 is a plan view of the apparatus in partly sectional form.
Figure 3:
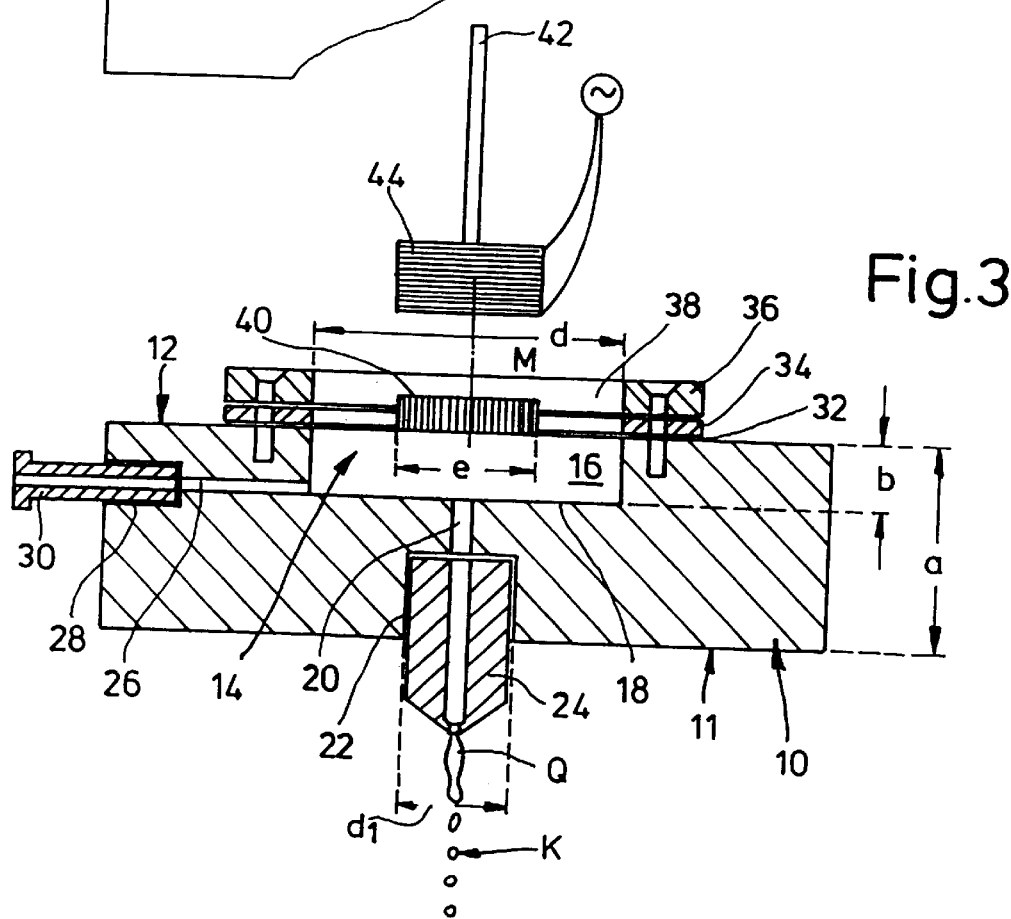
FIG. 3 is a view in section through FIG. 2 taken along line III—III therein.

Arranged in an installation (not shown) for the sterile encapsulation of microbial, vegetable and animal cells, above a hardening bath, is a for example rectangular carrier plate 10 of a thickness a, with a recess 14 which is formed in the center of its surface 12, the depth of the recess 14 being indicated at b; the latter approximately corresponds to one third of the plate thickness a.

The recess 14 is defined by a circular peripheral wall 16 of a diameter d and a bore 20 extends from the center point of its bottom 18. The bore 20 opens at the other end in a cup-shaped cavity 22 which is formed in the bottom surface 11 of the carrier plate 10, the diameter of the cavity 22 being indicated at $d_1$ (approximately one third of the dimension d). Disposed in the cavity 22 is a nozzle 24 which is connected to the bore 20. In addition, in the plane of the bottom 18, a radial duct 26 leads to a lateral blind hole 28 for a connecting portion 30.

Associated with the recess 14 is a pressure ring 36 which is fixed on the surface 12 of the plate, with the interposition of a diaphragm 32 and a seal 34; the pressure ring 36—like also the seal 34—has an internal opening 38 of a diameter d and the diaphragm 32 carrying a disk magnet 40 spans over the recess 14. The diameter e of the disk magnet 40 is somewhat longer than the diameter $d_1$ of the cavity 22 for the nozzle 24.

An electric coil 44 is suspended at a spacing relative to the disk magnet 40—in centered relationship with the center line M thereof—on a holder 42. The disk magnet 40 and the coil 44 through which alternating current flows form a vibrator: when alternating current is passed through the coil 44, it is alternately positively and negatively magnetized. The magnetic waves act on the disk magnet 40 disposed therebeneath and cause vibration thereof, together with the diaphragm 32.

An immobilization fluid is introduced through the radial duct 26 into the recess 14 which forms a pulsation chamber. The vibrations are transmitted to the immobilization fluid almost in a resistance-less condition. Introduction of the immobilization mixture is effected by means of a mechanical feed or by air pressure into the pulsation chamber or recess 14; from there the immobilization mixture is pressed through the nozzle 24. The jet Q which is produced there breaks up into equal-sized balls or spheres K shortly after issuing from the nozzle 24. according to the frequency of the superimposed vibration. At about 700 Hz, under optimum conditions. 700 equal-sized ball or spheres K are produced per second, with the homogeneity of the spherical configuration being excellent by virtue of the friction-less transmission. Measurements have shown that the power required is less than 0.2 W.

In an embodiment (not shown) the permanent magnet 40 or the coil 44 is provided directly at the nozzle 24 and the respective other unit is associated therewith, forming an air gap.

What is claimed is:

1. An apparatus for encapsulating a substance in small substantially spherical particles formed from an encapsulating fluid, said apparatus comprising:

a pulsation chamber containing a movable wall for receiving an encapsulating fluid containing a substance to be encapsulated;

a nozzle spaced downstream from the pulsation chamber for receiving the encapsulating fluid containing the substance to be encapsulated from the pulsation chamber;

a permanent magnet mounted on the movable wall of the pulsation chamber:

a coil spaced from the permanent magnet by an air gap and the coil being located proximate to the permanent magnet;

an alternating current source connected to the coil for creating an alternating magnetic wave of the permanent magnet to cause vibration of the permanent magnet and wall attached thereto to result in pulsing of the encapsulating fluid containing the substance to be encapsulated from the pulsation chamber and through the nozzle to encapsulate the substance in small substantially spherical particles formed from the encapsulating fluid.

2. An apparatus according to claim 1, wherein the alternating magnetic wave is in the range of between 300 to 4000 Hz.

3. An apparatus according to claim 1, wherein the substance is selected from the group consisting of microbial, vegetable, animal, biological, and chemical substances.

* * * * *